(12) United States Patent
Shokoohi

(10) Patent No.: US 9,827,077 B2
(45) Date of Patent: Nov. 28, 2017

(54) DENTAL PROPHY CUP

(71) Applicant: Cyrus Shokoohi, Marietta, GA (US)

(72) Inventor: Cyrus Shokoohi, Marietta, GA (US)

( * ) Notice: Subject to any disclaimer, the term of this patent is extended or adjusted under 35 U.S.C. 154(b) by 0 days.

(21) Appl. No.: 14/714,069

(22) Filed: May 15, 2015

(65) Prior Publication Data

US 2016/0331495 A1 Nov. 17, 2016

(51) Int. Cl.
*A61C 17/00* (2006.01)
*A61C 17/24* (2006.01)

(52) U.S. Cl.
CPC ............ *A61C 17/005* (2013.01); *A61C 17/24* (2013.01)

(58) Field of Classification Search
CPC ....... A61C 17/005; A61C 17/16; A61C 17/22; A61C 17/225; A61C 17/222; A61C 17/24; B43B 29/00; B43B 31/003; B43B 41/00; B43B 57/00; B24D 3/00; B24F 21/023
See application file for complete search history.

(56) References Cited

U.S. PATENT DOCUMENTS

| | | | | |
|---|---|---|---|---|
| 5,360,339 A | * | 11/1994 | Rosenberg | A61C 17/005 433/165 |
| 5,797,744 A | * | 8/1998 | Rosenberg | A61C 17/005 433/166 |
| 6,964,603 B2 | * | 11/2005 | Fischer | A61C 3/06 15/167.1 |
| 7,785,106 B2 | * | 8/2010 | Takahashi | A61C 3/06 433/125 |
| 8,784,102 B1 | * | 7/2014 | Kumar | A61C 1/141 433/116 |
| 2006/0166166 A1 | * | 7/2006 | Takahashi | A61C 3/06 433/125 |
| 2013/0067665 A1 | * | 3/2013 | Sowinski | A61C 17/228 15/4 |

* cited by examiner

*Primary Examiner* — Nicholas Lucchesi
*Assistant Examiner* — Shannel Wright

(57) ABSTRACT

The present invention relates to a dental prophy cup comprising a body, wherein the body comprising a rear portion adapted to be mounted on a rotary hand piece for rotation about a longitudinal axis; and a front portion for engaging the teeth, wherein the front portion is a microfiber surface provides for fluid communication between inner cavity and outer surface for exchange of prophy paste to clean the tooth surface.

5 Claims, 5 Drawing Sheets

DENTAL PROPHY CUP

The present invention relates to a dental prophy cup used in dental prophylaxis, in particular, to a novel configuration and construction of such a cup.

BACKGROUND OF THE INVENTION

A dental prophylaxis procedure typically involves the application of an abrasive paste (i.e., a paste containing abrasive particles) to a tooth surface upon which pressure and rotational motion are applied. The removal of plaque, calculus and stains is facilitated by the resultant abrasion at the interface between the abrasive particles and tooth surface.

The pressure and rotational motion are applied to the abrasive paste by means of a prophy cup which comprises a cup-shaped element of about one-quarter inch diameter, the outer peripheral wall of which is elastically flexible. The cup is mounted on a drive shaft which rotates the cup at high speed, e.g., about 1,500-5000 rpm. An operator presses the cup against a tooth following the insertion of abrasive paste into the cup. The paste serves as a carrier, and the abrasives in the paste function to abrade away plaque, calculus, and stains from the tooth surfaces.

This procedure has traditionally exhibited certain shortcomings. For example, during the prophylaxis procedure, the paste becomes diluted when coming into contact with saliva, blood and/or water. Since the amount of paste contained in the cup is small, e.g., about 0.1 grams, even a slight dilution has a pronounced adverse effect on the concentration of abrasive particles. As dilution increases, abrasion and performance decreases.

Additionally, the centrifugal force generated by a prophy cup rotating at about 1,500-5000 rpm causes the paste to be displaced in a radial direction. The amount of paste retained at the interface of the cup and tooth surface after one second (25 rotations) is a small fraction of the initial volume. The decreased amount of paste results in reduced abrasion and performance.

The above-described shortcomings involve a reduced availability of abrasive at the working area. Additional shortcomings, however, relate to the geometry of the cup. In that regard, prophy cups are designed to be flexible. That is, as the operator presses the cup against a tooth surface, the outer annular rim of the cup is intended to flex outwardly in order to increase the area of surface contact between the cup and the tooth. However, that the amount of flexing exhibited by presently used cups results in a relatively narrow area of surface contact being established. That area is ring-shaped. This makes it difficult for the operator to control the magnitude and placement of abrasion.

If the cup rim were made thinner in order to increase its flexibility, then the outer portion of the rim may apply only weak forces to the abrasive particles, whereby the cleaning action is ineffective.

Furthermore, conventional dental prophy cups spread germs over the teeth. They are not designed to lift off the germs from the teeth. Therefore, it would be desirable to provide a dental prophy cup which minimizes or obviates the above-described shortcomings.

BRIEF DESCRIPTION OF THE DRAWINGS

The objects and advantages of the invention will become apparent from the following detailed description of preferred embodiments thereof in connection with the accompanying drawings in which like numerals designate like elements and in which.

SUMMARY OF THE INVENTION

Figure 1:
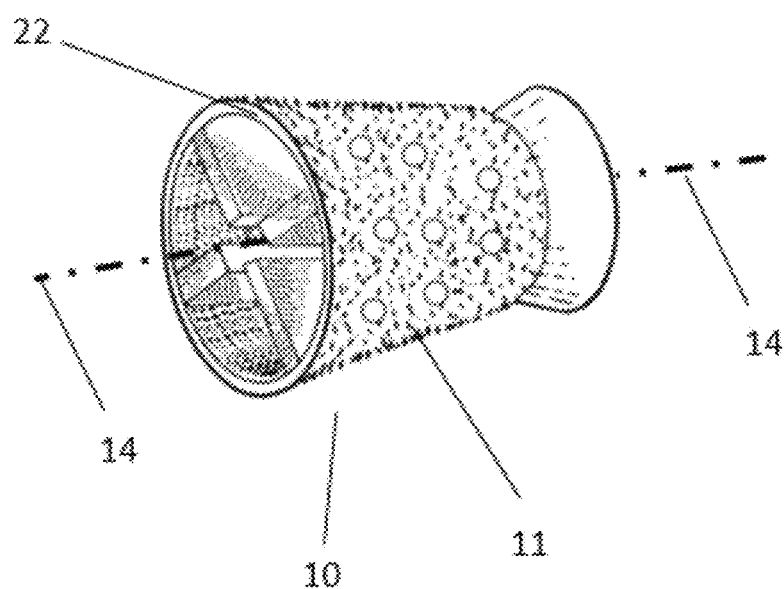
FIG. 1 is a perspective view of a dental prophy cup.
Figure 2:
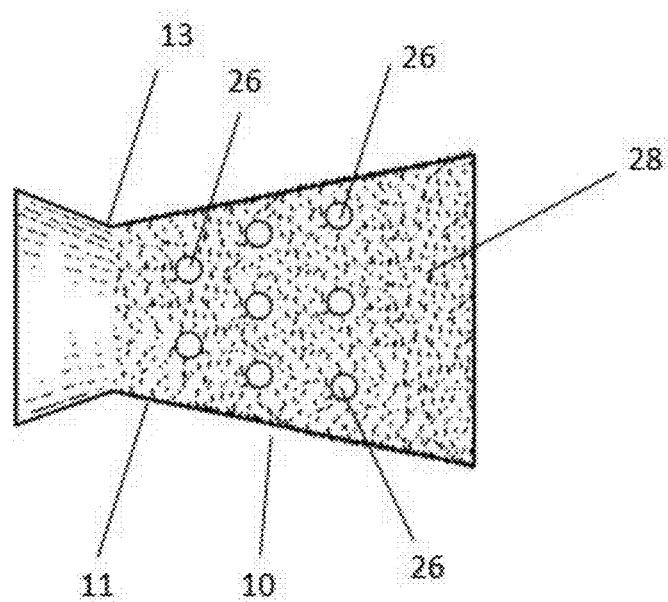
FIG. 2 is a side view of the dental prophy cup.
Figure 3:
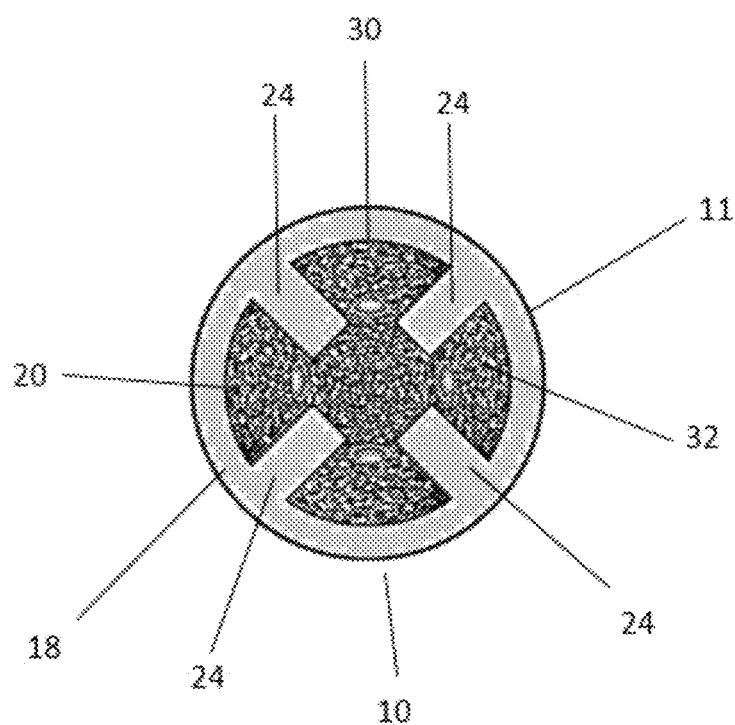
FIG. 3 is a front view of the dental prophy cup.
Figure 4:
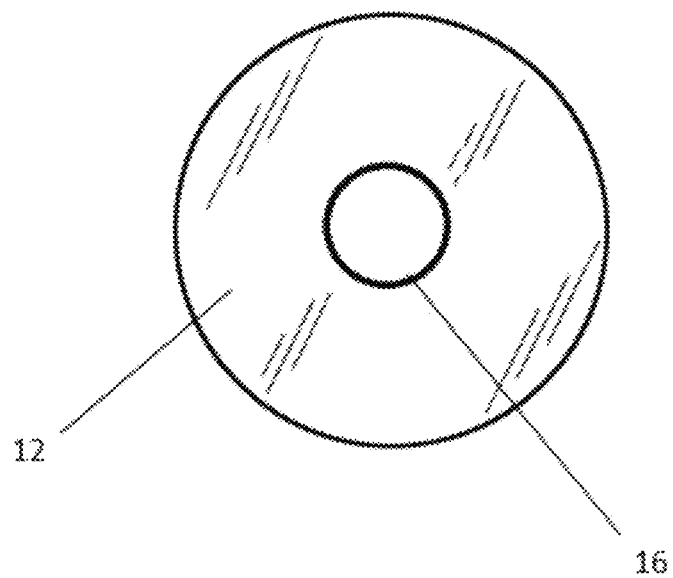
FIG. 4 is a rear view of the dental prophy cup.

The present invention relates to a dental prophy cup comprising a body, wherein the body comprising a rear portion adapted to be mounted on a rotary hand piece for rotation about a longitudinal axis; and a front portion for engaging the teeth, wherein the front portion is a microfiber surface.

Furthermore, the invention discusses a dental prophy cup comprising a body, wherein the body comprising a rear portion adapted to be mounted on a rotary hand piece for rotation about a longitudinal axis of rotation; a front portion formed of microfiber, wherein the front portion having a cavity for receiving an abrasive paste; and a plurality of channels that extend through annular wall of the front portion.

Moreover, the dental prophy cup comprising a body, wherein the body comprising a rear mounting portion adapted to be mounted on a rotary hand piece for rotation about a longitudinal axis of rotation; a front portion formed of microfiber, wherein the front portion having a cavity for receiving an abrasive paste; wherein the cavity comprising a plurality of ridges for engaging teeth; and a plurality of channels on a annular wall of the front portion that extend through the annular wall of the front portion, wherein the plurality of channels allows excess paste to exit from the cavity. The channels can also eliminate air being pocketed in the cup of the prophy cup.

DETAILED DESCRIPTION OF THE INVENTION

A dental prophy cup 10 depicted in FIGS. 1-4 comprises body 11. The body 11 comprises a rear portion 12 formed of a material such as plastic, metal, fiberglass, etc. The rear portion 12 is adapted to be mounted on a rotary hand piece (not shown) for rotation about a longitudinal axis of rotation of the prophy cup 10.

The rear portion 12 includes an adapter 16 for receiving, e.g., by press fit, a driving member of the rotary hand piece for rotating the body about its longitudinal axis of rotation. The adapter 16 may be a cavity, plug, screw, etc. for receiving the driving mechanism. The adapter 16 is configured to interface with the driving member. The driving member may be a shaft, rod, etc.

The body 11, which is configured symmetrically about the longitudinal axis of rotation 14, also includes a front portion 18. The front portion 18 is a tooth-engaging end. In some embodiments, the front portion 18 may be a flat surface or a concaved surface. In those embodiments, the flat or the concaved surface may be a microfiber surface. The microfiber surface will remove germs, instead of displacing them when engaging the tooth surface. In some embodiments the front portion 18 is made of flexible rubber-like material or silicon.

The front portion 18 and the rear portion 12 are connected via a narrow portion 13. Each of the aforementioned portions may be made of flexible rubber-like material, silicon, and/or microfiber.

In the present embodiment, the front portion 18 may comprise a cavity 20. The cavity 20 is configured to receive an abrasive paste therein. The cavity 20 is surrounded by an annular wall 22. A plurality of ridges 24 are placed on the interior side of the annular wall 22. The plurality of the ridges 24 are adapted to increase the abrasive character of the prophy cup 10. The cavity 20 and the ridges 24 further comprises a microfiber surface. This microfiber surface would allow for greater interaction with the tooth surface because the annular wall 22 and the cavity 20 will expand to form a large flat surface when the prophy cup 10 is pressured against the tooth surface. The greater interaction surface area created in this manner will allow for better removal of germs from the tooth surface.

The prophy cup 10 also includes a plurality of channels 26 defined through the annular wall 22. The plurality of channels 26 terminate at the cavity 20 at one end and terminate at the exterior surface 28 of the annular wall 22 at the opposing end.

In use, the cavity 20 is filled with an abrasive paste, the prophy cup 10 is pressed against a patient's tooth surface, and the prophy cup 10 is rotated. During the application of a slight force to the prophy cup 10, the front portion 18 flexes to cause the circumferentially continuous annular wall 22 and the interior of the cavity 20 of the front portion 18 and its ridges 24 to contact the tooth surface which is from small to moderate curvature.

It will be appreciated that the flexing of the prophy cup 10 is facilitated by the presence of the grooves 30 which reduce the thickness of the cup body and define annular bending fulcrums about which certain portions of the prophy cup 10 can flex in order to enable the cavity surfaces 32 into engagement with the tooth surface. In other words, the prophy cup 10 is better able to conform to the curvature of the tooth surface. As the prophy cup 10 rotates, the abrasive paste compressed between the prophy cup 10 and tooth abrades away stains and adherent materials such as plaque. Further, the microfiber surface of the prophy cup 10 will lift of plaque and germs from the tooth surface.

Moreover, centrifugal force causes the abrasive paste to travel radially outwardly, and thus longitudinally forwardly, due to the forwardly expanding shape of the cavity surface 32. Some of the extra paste disposed within the cavity 20 is quickly expelled from the plurality of channels 26.

Furthermore, by increasing the paste retention time and distribution, and enhancing the area of tooth contact, the overall abrasiveness (and thus effectiveness) of the prophy cup 10 is increased.

In some embodiments of the present invention, the exterior of the prophy cup 10 includes ridges that which do not cause kicking or skidding on the tooth surface when spinning clockwise or counter-clockwise. In those embodiments, the outer surface of the prophy cup 10 can have any other designs that will accommodate batter prophy application, as the outer surface of the prophy cup 10 is not limited to ridge lines. For example, the ridges of the outer surface of the prophy cup 10 can be made horizontally or combination of mixed geometric designs without hindering the function of the prophy cup itself.

Figure 5:
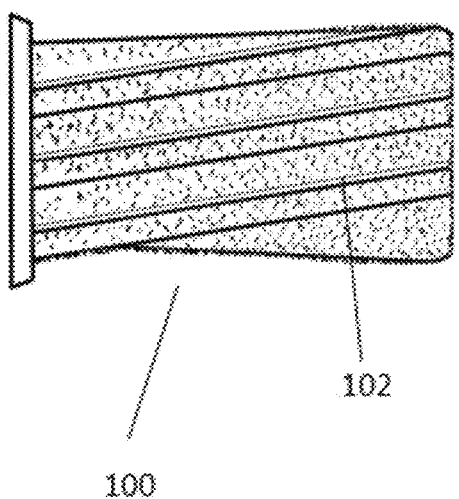
FIG. 5 is a side view of an embodiment of a dental prophy cup.

In one exemplary embodiment, as shown in FIG. 5, an exemplary prophy cup 100 includes a plurality of grooves 102 spiraling on the outer surface of the exemplary prophy cup 100. This embodiment may be made of silicon or similar material. Furthermore, the prophy cup may be made of microfiber.

Furthermore, the shape of the exemplary prophy cup 100 may be adapted to the form a cone shape, such that the front portion of the prophy cup 100 will be a pointy end and the rear portion will be a circular end. The exterior of the prophy cup will include ridges 102 extending between the front and rear portions.

In some embodiments, the exterior or inner surfaces of the prophy cup may include miniature geometrical elevations and ridges. Those ridges may be form a swirl like ridges on either or both exterior on interior surfaces of the prophy cup.

In some embodiments, the channels provide a means for fluid communication between inner cavity and the outer surface. The channels may be formed by defining a slit into the annular wall where the slit opens when the prophy cup is pressed against the teeth. In some embodiment a combination of slit and holes may be used on the annular wall.

Although the present invention has been described in connection with preferred embodiments thereof, it will be appreciated by those skilled in the art that additions, deletions, modifications, and substitutions not specifically described may be made without departing from the spirit and scope of the invention as defined in the appended claims.

The invention claimed is:

1. A dental prophy cup comprising:
a body, wherein the body comprising a rear portion adapted to be mounted on a rotary hand piece for rotation about a longitudinal axis; and a front portion comprising grooves defining annular bending fulcrums about which certain portions of the prophy cup can flex in order to enable the front portion into engagement with a tooth surface, wherein the front portion is a microfiber surface; the front portion further comprising a cavity for receiving an abrasive paste, wherein the cavity comprises a plurality of channels extending through an annular wall of the front portion and the plurality of channels formed by defining a slit into the annular wall where the slit opens when the prophy cup is pressed against the tooth surface allowing excess paste to exit from the cavity.

2. The dental prophy cup of claim 1, wherein the cavity further comprising a plurality of ridges for engaging a tooth surface.

3. The dental prophy cup of claim 1, wherein a portion of the body is made of flexible elastomeric material.

4. The dental prophy cup of claim 1, wherein the prophy cup has a narrow portion between the front portion and the rear portion.

5. The dental prophy cup of claim 1, wherein the body is formed of silicone and microfiber.

* * * * *